United States Patent [19]
Lesinski

[11] Patent Number: 5,984,859
[45] Date of Patent: *Nov. 16, 1999

[54] IMPLANTABLE AUDITORY SYSTEM COMPONENTS AND SYSTEM

[76] Inventor: S. George Lesinski, 324 Bishopsbridge Dr., Cincinnati, Ohio 45255

[ * ] Notice: This patent issued on a continued prosecution application filed under 37 CFR 1.53(d), and is subject to the twenty year patent term provisions of 35 U.S.C. 154(a)(2).

[21] Appl. No.: 08/637,854

[22] Filed: Apr. 25, 1996

Related U.S. Application Data

[63] Continuation of application No. 08/008,663, Jan. 25, 1993, Pat. No. 5,531,787.

[51] Int. Cl.$^6$ .............................. H04R 25/00; A61F 2/18; A61B 19/00
[52] U.S. Cl. .............................. 600/25; 623/10; 128/898; 607/57
[58] Field of Search .............................. 660/25; 623/10; 607/55, 56, 57; 128/642, 898; 381/153, 154, 162, 68.3, 68.6

[56] References Cited

U.S. PATENT DOCUMENTS

| | | | |
|---|---|---|---|
| 31,031 | 9/1861 | Kissiah, Jr. | 179/107 R |
| 3,346,704 | 10/1967 | Mahoney | 179/107 |
| 3,557,775 | 1/1971 | Mahoney | 128/1 |
| 3,594,514 | 7/1971 | Wingrove | 179/107 R |
| 3,712,962 | 1/1973 | Epley | 179/107 R |

(List continued on next page.)

FOREIGN PATENT DOCUMENTS

| | | | |
|---|---|---|---|
| 0076069A1 | 4/1983 | European Pat. Off. . | |
| 0259906A1 | 3/1988 | European Pat. Off. . | |
| 0563767 | 10/1993 | European Pat. Off. | 623/10 |
| 2688132 | 9/1993 | France | 623/10 |
| 1551371 | 3/1990 | U.S.S.R. | 623/10 |
| 9000040 | 1/1990 | WIPO | 623/10 |
| 9007915 | 7/1990 | WIPO | 623/10 |

OTHER PUBLICATIONS

"How I Do It"–Otology and Neurotology, Laryngoscope 93: Jan. 1983, pp. 824–825.
Lasers in Revision Stapes Surgery, S. George Lesinski, M.D., Janet A. Stein, Head and Neck Surgery, vol. 3, No. 1 (Mar.) 1992, pp. 21–31.
Lasers for Otosclerosis—Which One if Any and Why, S. George Lesinski, M.D.
Lasers in Surgery and Medicine 10:448–457 (1990).
Lasers for Ostoclerosis, S. George Lesinski, M.D., The Laryngoscope, Supplement No. 46, Jun. 1989, vol. 99, No. 6, Part 2, pp. 1–24.
Homograft (Allograft) Tympanoplasty Update, S. George Lesinski, M.D., Laryngoscope, vol. 96, No. 11, Nov. 1986.
Reconstruction of Hearing when Malleus Is Absent: Torp vs. Homograft TMMI, S. George Lesinski, M.D., Laryngoscope, vol. 94, No. 11, Nov. 1984.
Homograft Tympanoplasty in Perspective, A Long–Term Clynical–Histologic Study of Formalin–Fixed Tympanic Membranes Used for the Reconstruction of 125 Serverely Damaged Middle Ears, S. George Lesinski, M.D., The Laryngoscope, Supplement No. 32—Vol. 93, No. 11, Part 2, Nov. 1983, pp. 1–37.

(List continued on next page.)

*Primary Examiner*—Debra S. Brittingham
*Assistant Examiner*—Jeffrey R. Jastrzab
*Attorney, Agent, or Firm*—Donald E. Schreiber

[57] ABSTRACT

Auditory system components and system adapted for implantation into a human subject for reducing conductive and/or sensorineural hearing deficiency in the subject. An electrically excitable microactuator is implantable either into a fenestration formed through a promontory or a stapes footplate which respectively separate a middle ear from an inner ear of the human subject. The auditory system also includes an implantable processor for supplying an electrical signal to the microactuator, and an implantable microsensor for transmitting an electrical signal responsive to impingement of sound on the microsensor.

5 Claims, 7 Drawing Sheets

U.S. PATENT DOCUMENTS

| | | | |
|---|---|---|---|
| 3,764,748 | 10/1973 | Branch et al. | 179/107 E |
| 3,870,832 | 3/1975 | Frederickson | 179/107 E |
| 3,882,285 | 5/1975 | Nunley et al. | 179/107 E |
| 4,063,048 | 12/1977 | Kissiah | 179/107 R |
| 4,284,856 | 8/1981 | Hochmair et al. | 179/107 E |
| 4,498,461 | 2/1985 | Hakansson | 128/1 R |
| 4,617,913 | 10/1986 | Eddington | 128/1 R |
| 4,729,366 | 3/1988 | Schaefer | 128/1.6 |
| 4,817,607 | 4/1989 | Tatge | 128/419 R |
| 4,817,609 | 4/1989 | Perkins et al. | 128/419 R |
| 4,850,962 | 7/1989 | Schaefer | 600/25 |
| 4,908,509 | 3/1990 | Senturia | 356/373 |
| 4,928,264 | 5/1990 | Kahn | 367/141 |
| 4,943,750 | 7/1990 | Howe et al. | 310/309 |
| 4,957,478 | 9/1990 | Maniglia | 600/25 |
| 4,988,333 | 1/1991 | Engebretson et al. | 625/25 |
| 5,015,224 | 5/1991 | Maniglia | 600/25 |
| 5,015,225 | 5/1991 | Hough et al. | 600/25 |
| 5,033,999 | 7/1991 | Mersky | 600/25 |
| 5,061,282 | 10/1991 | Jacobs | 623/10 |
| 5,070,535 | 12/1991 | Hochmair | 455/41 |
| 5,085,628 | 2/1992 | Engebretson et al. | 600/25 |
| 5,095,904 | 3/1992 | Seligman et al. | 128/420.6 |
| 5,165,897 | 11/1992 | Johnson | 434/113 |
| 5,176,620 | 1/1993 | Gilman | 600/25 |
| 5,180,391 | 1/1993 | Beoni | 623/10 |
| 5,271,397 | 12/1993 | Seilgman et al. | 607/137 |
| 5,277,694 | 1/1994 | Leysieffer et al. | 600/25 |
| 5,282,858 | 2/1994 | Bisch et al. | 623/10 |
| 5,304,431 | 4/1994 | Schumm, Jr, | 429/27 |
| 5,306,299 | 4/1994 | Applebaum | 623/10 |
| 5,318,502 | 6/1994 | Gilman | 600/25 |
| 5,411,467 | 5/1995 | Hortmann et al. | 600/25 |
| 5,449,569 | 9/1995 | Schumm, Jr. | 429/27 |
| 5,498,226 | 3/1996 | Lenkauskas | 600/25 |
| 5,531,787 | 7/1996 | Lesinski et al. | 623/10 |

OTHER PUBLICATIONS

Microfabrication Techniques for Integrated Sensors and Microsystems, K. D. Wise, et al., Science, vol. 254, Nov. 1991, pp. 1335–1341.

Hearing Aids: A Historical and Technical Review, W. F. Carver, Ph.D., Jack Katz, PH.D., Handbook of Clinical Audiology, 1972, pp. 564–576.

Implantable Hearing Devices–State of the Art. Anthony J. Maniglia. M.D., Otolaryngologic Clinics of North America, vol. 22, No. 1, Feb. 1989, pp. 175–200.

Current Status of Electromagnetic Implantable Hearing Aids, Richard L. Goode, M.D., Otolaryngologic Clinics of North America, vol. 22, No. 1, Feb. 1989, pp. 201–209.

History of Implantable Hearing Aid Development: Review and Analysis, John M. Epley, edited by I. Kaufman Arenberg, Kugler Publications 1991.

Proceeding of the Third International Symposium and Workshops on the Surgery of the Inner Ear, Snomass, CO, USA, Jul. 29–Aug. 4, 1990.

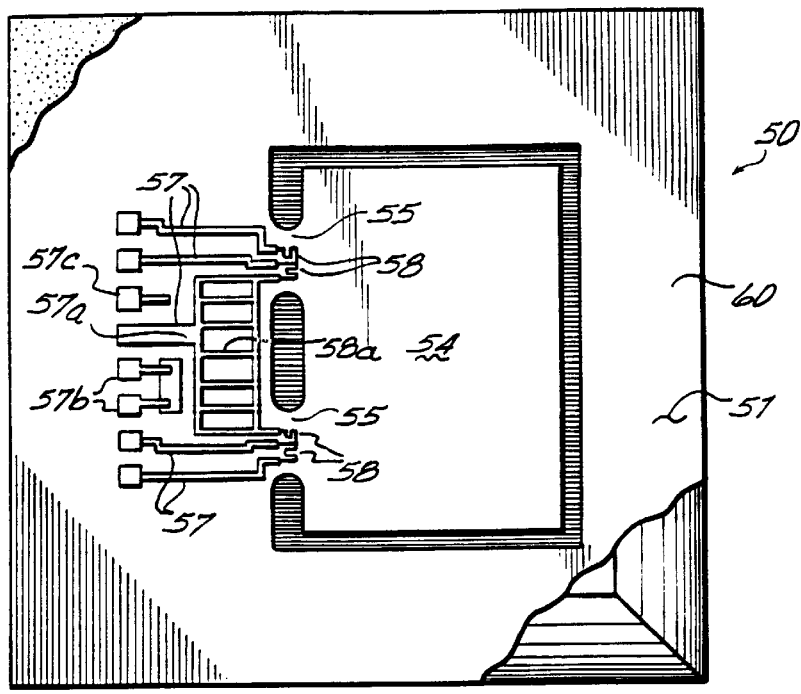
FIG. 3A
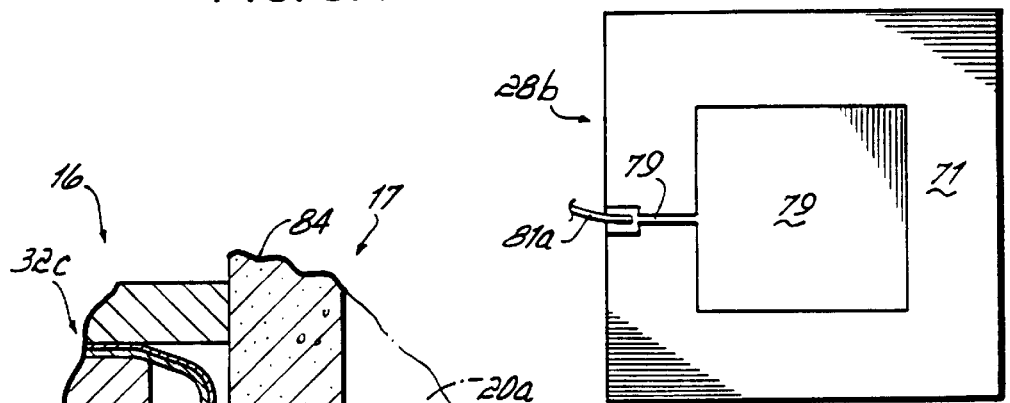
FIG. 4A
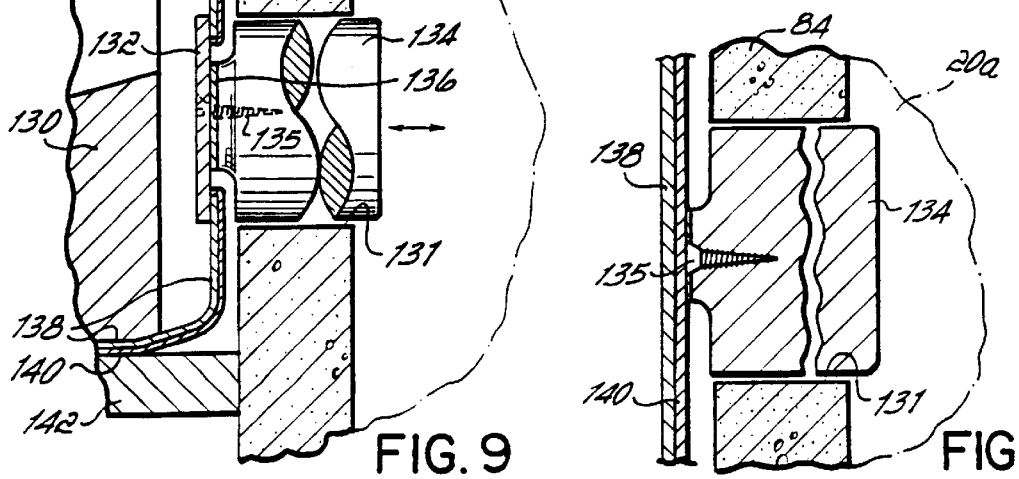
FIG. 9
FIG. 9A

IMPLANTABLE AUDITORY SYSTEM COMPONENTS AND SYSTEM

This is a continuation of application Ser. No. 08/008,663 filed Jan. 25, 1993, now U.S. Pat. No. 5,531,787.

FIELD OF THE INVENTION

This invention relates to an implantable auditory system for improving the hearing capability of: a human subject with conductive and/or sensorineural hearing deficiency.

BACKGROUND OF THE INVENTION

In normal human hearing, acoustical energy in the form of sound waves is directed into the ear canal of a human by the outer ear. The sound waves impinge upon a tympanic membrane, i.e. the eardrum, located at the inner end of the outer ear canal. The pressure of the sound waves causes tympanic vibrations in the eardrum, thereby producing mechanical energy.

Three interconnected bones referred to as the ossicular chain transfer these tympanic vibrations of the eardrum across the middle ear and into the inner ear. The ossicular chain includes three major bones, the malleus, the incus and the stapes. The stapes terminates at a membrane referred to as the oval window, which serves as the outer boundary for the inner ear.

Mechanical vibrations conducted to the oval window generate fluidic motion within the inner ear. A spiral shaped portion of the inner ear, referred to as the cochlea, includes auditory receptor cells connected to the ends of auditory nerve fibers. Fluid vibrations within the inner ear actuate the receptor cells, thereby causing the nerve fibers to transmit signals to the brain which are perceived by the subject as sound.

Generally, hearing difficulties fall into one of two categories. Conductive hearing loss relates to the inability, or inefficiency, in mechanically conveying the vibrations caused by sound waves through the outer ear, the middle ear and the oval window to the fluid of the inner ear. Sensorineural hearing impairment relates to deterioration of the receptor cells and/or nerve fibers within the inner ear, so that fluidic vibrations within the inner ear are not sensed at all, or are sensed at a lower magnitude.

Over the years, various devices or aids have been developed to improve the hearing of hearing impaired individuals. One such device is generally referred to as an externally worn hearing aid. This device amplifies processed sound waves in the external ear canal. While it has been estimated that 20% of hearing-impaired individuals have purchased a hearing aid, it is also reported that less than one-half of these individuals wear their hearing aids regularly.

Externally worn hearing aids suffer from several inherent problems which result in distorted hearing and a poorly tolerated device. First, the amplifying of sound waves in the external ear canal while the external canal is obstructed with a hearing aid produces constructive and destructive acoustical wave interference. This interference results in resonance of some frequencies, cancellation of other frequencies and distortion of the remaining acoustical waves.

Second, because of the relative proximity of the hearing aid microphone and speaker, acoustical feedback is a constant problem, producing "whistling and screeching" of the hearing aid when amplification is turned up. The more amplification required, the worse this problem becomes. While some hearing aids employ a tight-fitting mold to reduce this feedback, such a mold is usually uncomfortable, and often ulcerates the skin of the ear canal or produces autophony, i.e. the hearing by a patient of his or her own voice in that ear. Moreover, radiation of acoustical output back into the microphone via the hearing aid case or the hearing aid internal components further limits the gain/output of an externally worn hearing aid.

Third, these hearing aids provide only limited amplification, due primarily to the limited power from a hearing aid battery. Commercially available in-the-ear and behind-the-ear hearing aids amplify sound by a magnitude of about 30–70 dB.

Fourth, distortion of hearing aids is high. Compared with radios, stereo sets and other electronic devices, the electronic distortion of hearing aids is enormous. Average commercially available hearing aids have a total harmonic distortion of 2–25%. Transient and intermodulation distortion produce further acoustical problems. The signal-to-noise ratio of commercially available hearing aids is vastly inferior to even inexpensive sound systems.

Because of this acoustical and electronic distortion, signal processing is usually required in the form of band pass filters, noise suppression circuits, etc. These electronic circuits further drain the power source and limit amplification.

Fifth, externally worn hearing aids cannot be safely worn by a significant number of individuals whose hearing is impaired by diseases which affect the external ear canal or middle ear, such as congenital aural atresia with absent ear canal, external otitis, chronic otitis media, mastoiditis, eardrum preformation, etc.

Sixth, externally worn hearing aids cannot be effectively worn when playing contact sports, perspiring excessively, swimming, showering, working in excessive noise and in many other conditions.

Finally, externally worn hearing aids often carry a social stigma, particularly in children. This social distinction can adversely affect a child's positive self esteem.

As a result of these problems, a number of semi-implantable hearing devices have been developed. These hearing devices actuate the inner ear either electromagnetically or by a piezoelectric bimorph lever. However, after nearly thirty years of attempts to develop a practical electromagnetically or piezoelectrically actuated hearing aid, to applicant's knowledge, none of these devices have yet been approved in the United States by the FDA. This lack of success is the result of problems inherent in each of these approaches, problems which have not yet been solved.

Electromagnetic actuation devices have been unsuccessful for several reasons. First, the strength of the magnetic field which actuates the ear is directly dependent on the amount of current flowing through the magnetic coil and the number of turns in the coil. Thus, high current and/or a coil with an extremely large number of turns is required. For a conventionally sized coil, this high current requirement rapidly drains battery power, exhausting a conventionally sized battery source within several hours.

Second, the amount of amplification produced in the core magnet is approximately inversely proportional to the square of the distance between the induction coil and the core magnet. Third, these electromagnetic actuation devices may be susceptible to stray magnetic fields. Finally, in clinical trials in the United States, optimum amplification of electromagnetic actuation devices has been in the range of only about 30–40 dB.

The inherent flaw with piezoelectric bimorph lever relates to size. More specifically, a lever of unrealistic length is necessary to attain adequate amplitude of sound vibrations to stimulate the middle ear ossicles. The middle ear is simply too small to accommodate the necessary piezoelectric lever length.

Presently, in Japan, surgeons are attempting to inertially anchor a piezoelectric bimorph lever in the mastoid. However, these procedures require major destructive otologic surgery, including radical mastoidectomy and closure of the ear canal. To the extent that the implanting of such devices requires destructive procedures, these devices are not likely to be approved in the United States by the Food and Drug Administration.

Perhaps more importantly, to the extent that implantable devices or procedures of this type do not result in improved hearing, the situation is irreversible, and the subject will most likely have lost any opportunity for hearing improvement by other implantable devices or surgical procedures.

It is an objective of this invention to overcome the present problems associated with commercially available, externally worn hearing aids via an auditory system which is sufficiently safe and reliable to achieve F.D.A. approval.

It is another objective of the invention to develop an implantable auditory system, and particularly an actuation device, with reduced electrical power requirements, better acoustical amplification, and which is small enough to eliminate the need for major and/or destructive surgical procedures.

It is still another object of the invention to develop an implantable auditory system with a high probability of success in overcoming a subject's conductive and/or sensorineural hearing deficiency, but which does not cause irreversible hearing loss in the subject if the system should wear out or prove to be unsuccessful.

The above-stated objectives are achieved by an implantable auditory system which comprises a micromachined microsensor and a micromachined microactuator which are very small, yet which provide up to 100 dB of amplification. Because of the small size, surgical implanting of these components within the middle ear of a subject requires no destructive and/or irreversible surgical procedures.

To the contrary, present surgical techniques, including laser surgery, may be used to implant these micromachined components. In fact, according to one embodiment of the invention, the micromachined actuator employed by this auditory system may be incorporated into the bottom of a piston-like prostheses which is extended through the stapes footplate in present stapedotomy techniques.

The auditory system of this invention is an integrated, fully implantable micro system which improves hearing in patients with conductive and/or sensorineural deafness. This auditory system utilizes silicon semiconductor microfabrication and micromachining techniques to produce integrated components which amplify hearing by electrostatically stimulating the fluid of the inner ear. Because of the size and configuration of the micromachined components, particularly the microactuator, which acts as a parallel plate capacitor, small voltage changes produce large electric fields which are used to vibrate the fluid of the inner ear.

According to the invention, the major components of this auditory system include a microsensor and a microactuator implanted in the middle ear of the subject and a signal processor, amplifier, and power source implanted subcutaneously in the cortical mastoid bone.

The microsensor is either a micromachined piezoresistive vibration sensor, a micromachined parallel plate capacitor, or a micromachined acoustical microphone designed and produced using microfabrication techniques and having a mass of less than about 30 grams. The microsensor senses acoustical pressure waves produced in the middle ear by mechanical vibrations of the eardrum or mechanical vibrations of one of the bones of the ossicular chain, and it converts the sensed waves or vibrations into electrical signals. The microsensor may be secured to one of the bones of the ossicular chain, preferably the incus. Alternatively, particularly for those individual subjects who suffer from congenital aural atresia, wherein the external canal is absent, the microsensor may be planted subcutaneously in the mastoid cortical bone behind the ear. If desired, the microsensor may be combined as an integral piece with the micromachined microactuator. As yet another alternative, the sensor may be inserted into the incudostapedial joint, i.e. the joint between the incus and the stapes, and used to sense the pressure therebetween.

After the microsensor converts sensed mechanical vibrations into electrical signals, the electric signals pass from the microsensor through the facial recess to a signal processor, which includes a signal conditioner, an amplifier, and a power source. The conditioned and amplified signal is then transmitted back to the microactuator located in the middle ear, which includes a flexible dielectric or semiconductive diaphragm on a semiconductor substrate that transduces the electrical signals back into mechanical vibrations to directly stimulate the perilymph fluid of the cochlea through a fenestration in the promontory or the stapes footplate. Alternatively, the diaphragm of the microactuator mounts to a piston which resides in contact with the incus or the stapes so that vibrations of the diaphragm and piston amplify the vibrations of the incus or the stapes, respectively, thereby indirectly stimulating the perilymph fluid. This latter alternative avoids the necessity of surgically entering the inner ear. This implanted auditory microsystem does not rely on amplification of sound waves in the external ear canal, and thus eliminates the substantial acoustical and electronic distortion created by present day externally worn hearing aids.

The microactuator is preferably a micromachined parallel plate capacitor with a major portion of a semiconductor crystal serving as one stationary plate and a flexible monolithic dielectric or semiconductive diaphragm spaced about 1–5 microns away from the major portion, with the spacing or void therebetween formed by etching. A metallized coating deposited on the exterior surface of the diaphragm may serve as the other "plate". Alternatively, if mounted in a fenestration in the promontory or stapes footplate and in contact with the perilymph, which is inherently electrically conductive, the perilymph may serve as the other "plate". The crystal may be doped. The doping of the crystal will dictate the etchants to be used in micromachining this capacitor.

Because of the extremely small thickness of the diaphragm and the void, voltage changes conveyed to the microactuator produce extremely high electric fields across the "plates" of the micromachined capacitor. The resultant electrostatic forces acting upon the plates cause the diaphragm to flex. By locating the microactuator in a position where the diaphragm movements can vibrate the fluid of the inner ear, voltage changes conveyed to the micromachined microactuator actuate the auditory receptor cells to cause the associated nerve fibers to signal the brain to perceive sound.

According to one approach, the flexible diaphragm is a dielectric which resides in direct contact with the perilymph fluid of the inner ear. According to this approach, the microactuator is housed within a screw which is threaded through a promontory fenestration formed via laser or other surgery techniques. The diaphragm is located at the end of the screw. The external surface of the screw serves as one electrode, and contact between the inserted end of the screw and the ionic perilymph fluid causes the perilymph fluid to act as one conductive plate which resides in direct contact with the flexible dielectric diaphragm.

An electrical lead extended through the screw conveys electrical voltage signals to the stationary plate of the microactuator, i.e., the major portion of the semiconductor crystal, which is spaced from the flexible diaphragm. When using this approach, it is important to electrically insulate the doped semiconductor material, which serves as the stationary plate of the microactuator, from the electrically conductive portions of the screw. This may be accomplished via a glass coating on the inside of the metal screw, or the use of a teflon screw coated on its external surface with an electrically conductive and biocompatible material such as gold.

This approach may also be used with a piston, rather from a screw, and by forming the fenestration in the stapes footplate, as in present stapedotomy techniques. In this present stapedotomy technique, passive sound transmission to the inner ear is achieved via mechanical vibration of a prostheses surgically extending through the fenestration in the footplate. One embodiment of the present invention modifies this prostheses by housing a micromachined capacitor in a piston extending into a fenestration in the footplate. Electronic actuation of the capacitor vibrates the diaphragm to amplify the vibrations of the piston. In this approach, if the electronics should happen to fail, the subject is no worse off because the mechanical piston, similar to presently used prostheses, is still in place.

Alternatively, the microactuator may be located in a micromachined semiconductor housing which is tapered to fit within a tapered fenestration in the promontory. In this approach, the flexible diaphragm may carry a conductive coating to serve as one of the plates, but preferably this perilymph is again used as the outer plate.

As another alternative, which is most applicable to a fenestration formed in the promontory, the diameter of the diaphragm may be increased and/or the diameter of the fenestration may be reduced by connecting the flexible diaphragm to a piston and locating the diaphragm outside of the inner ear and the piston inside the inner ear.

As yet another approach, the microactuator may be mounted to the incus or the stapes, and inertially grounded to the promontory if desired, so that movement of the flexible semiconductive diaphragm amplifies movement of the ossicular chain and thereby indirectly vibrates the perilymph fluid of the inner ear.

This inventive auditory system is made possible only because of the small geometries attainable with the revolutionary "micromachining" processes which may be applied to single crystalline <100> oriented semiconductor silicon. With a microactuator formed by micromachining and having dimensions and geometries that are this small, i.e. in the micrometer range, a relatively small voltage of a few volts can produce an enormous electrical field intensity which is entirely contained within the microactuator. As a result, strong electrostatic forces are generated which achieve a high degree of acoustical actuation in the very small spaces available in the middle ear and inner ear of a subject. Moreover, because this acoustical actuation is achieved via electrostatic forces produced by a micromachined capacitor, which uses only minimum electrical current, battery life for this auditory system is much longer than prior implantable systems. Preliminary studies indicate that an implanted five or six volt battery used to electrically drive the components of this auditory system can last up to four to five years.

Moreover, unlike implanted devices which rely upon electromagnetic actuation, stray magnetic fields can be expected to have virtually no effect on this auditory system. Likewise, stray electrical fields will have absolutely no effect on this system because the intensity of such stray electric fields will be several orders of magnitude lower than the intensity of the electric field produced in the electric fields generated in the microactuator used in this auditory system.

These and other features of the invention will be more readily understood in view of the following detailed description and the drawings.

BRIEF DESCRIPTION OF THE DRAWINGS

FIG. 3A is a top schematic view of the microsensor of FIG. 3.

FIG. 4A is a top elevational view of FIG. 4.

FIG. 9 is a cross-sectional schematic which depicts a third preferred embodiment of a microactuator for directly vibrating the fluid of the inner ear in accordance with the invention.

FIG. 9A is a cross-sectional schematic which depicts a variation of the embodiment of the microactuator shown in FIG. 9.

DETAILED DESCRIPTION OF THE DRAWINGS

I. The General System

Figure 1:
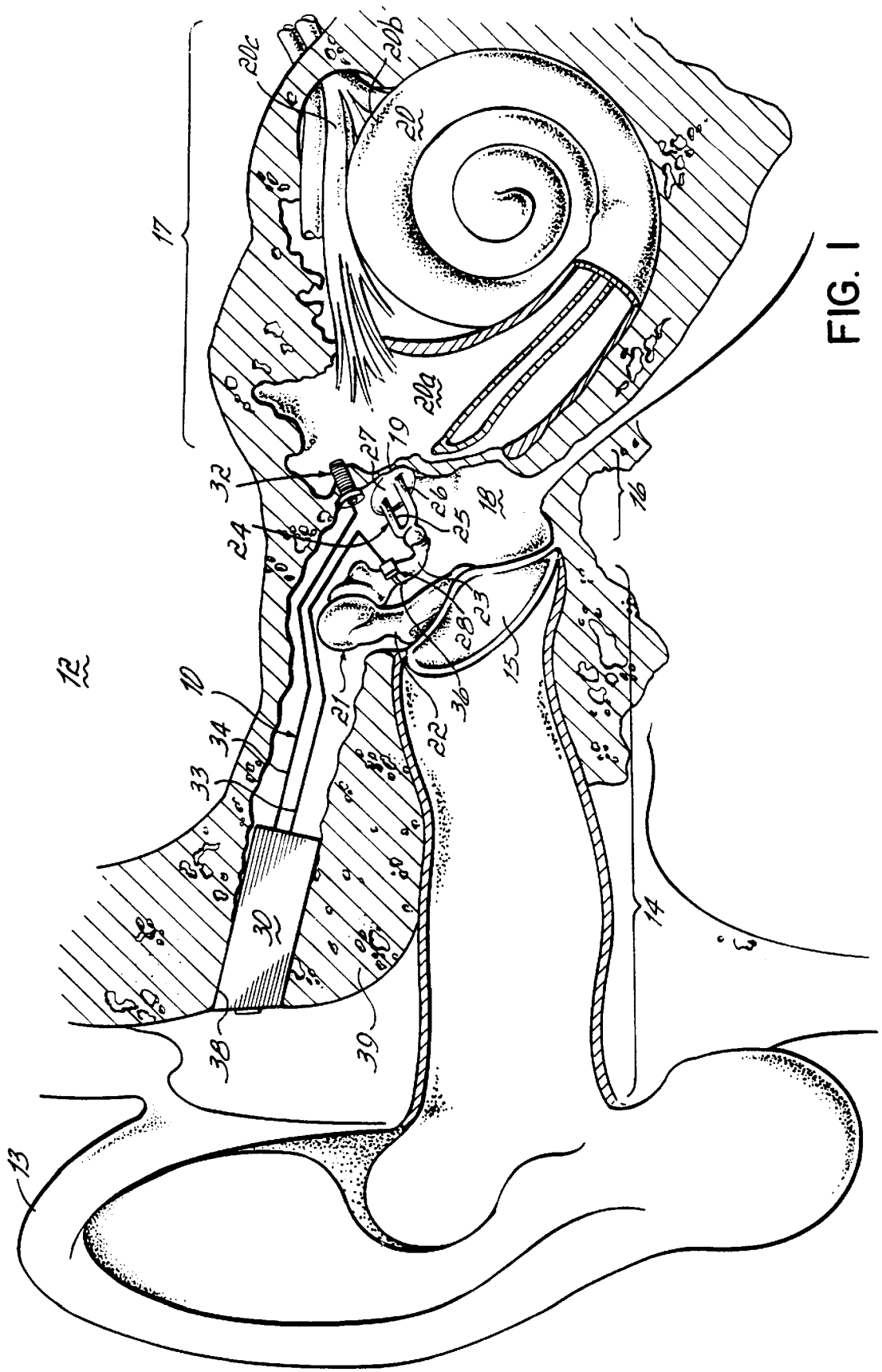
FIG. 1 is a schematic sectional view through a portion of the skull of a human subject adjacent the ear and showing the relative positions of the components of an implantable auditory system constructed in accordance with the invention.

FIG. 1 shows the relative locations of the components of an implantable auditory system 10 constructed in accordance with this invention and implanted in the body of a human subject 12. FIG. 1 shows an external ear 13 of the subject 12 located at the outer end of the outer ear 14. The outer ear 14 terminates at the ear drum 15. The ear drum 15 is a tympanic membrane which mechanically vibrates in response to sound waves that travel through the outer ear 14. The ear drum 15 serves as a barrier between the outer ear 14 and the middle ear 16. The inner ear 17 is located inside the middle ear 16. A relatively large bone referred to as the promontory 18 separates the inner ear 17 from the middle ear 16. The promontory 18 includes an oval shaped window 19. The inner ear 17 includes a shell-shaped organ called the cochlea 20.

A labyrinth of bones referred to as the ossicular chain 21 spans the middle ear 16 to inner-connect the ear drum 15 with the middle ear 17, at the oval window 19. The ossicular chain 21 conveys the mechanical vibrations of the ear drum 15 to the inner ear 17, thereby causing fluidic vibrations in the perilymph fluid 20a contained in the cochlea 20. Vibrations in the perilymph fluid of the cochlea 20 actuate receptor cells 20b which cause nerve fibers 20c to signal the brain (not shown) of the subject 12 to perceive the vibrations as sound. The ossicular chain 21 includes the malleus 22, the incus 23 and the stapes 24. The stapes 24 includes leg portions 25 and 26 shaped similar to a wishbone and a footplate 27 which covers the oval window 19.

FIG. 1 also shows the three major components of auditory system 10, a microsensor 28, a processor 30 and a microactuator 32. A miniaturized electrical cable 33 interconnects the microsensor 28 with the processor 30, and a miniaturized electrical cable 34 interconnects the processor 30 with the microactuator 32. The microsensor 28 is mounted adjacent the eardrum 15 and is preferably secured to the incus 23 by a crimped wire or hook 36. The microsensor 28 senses mechanical vibrations of the eardrum 15 and/or one of the bones of the ossicular chain 21 and converts the sensed vibrations into electrical signals which are conveyed along cable 33 to processor 30.

The processor 30 is implanted subcutaneously behind the external ear 13 within a hole 38 surgically sculpted in the mastoid cortical bone 39 of the subject 12. The processor 30 conditions the electrical signals. More specifically, the processor 30 separates the electrical signals into a predetermined number of bandwidths, translates the electrical signals plus or minus one hundred and eighty degrees into proper phase, amplifies the electrical signals and then conveys the conditioned electrical signals along cable 34 to the microactuator 32. The microactuator 32 transduces the electrical signals to mechanical vibrations to directly or indirectly vibrate the perilymph fluid 20a in the inner ear 17, thereby actuating the receptor cells 20b to cause the nerve fibers 20c to signal the brain of the subject 12 to perceive the initial mechanical vibrations in the outer ear 14 as sound.

Figure 1A:
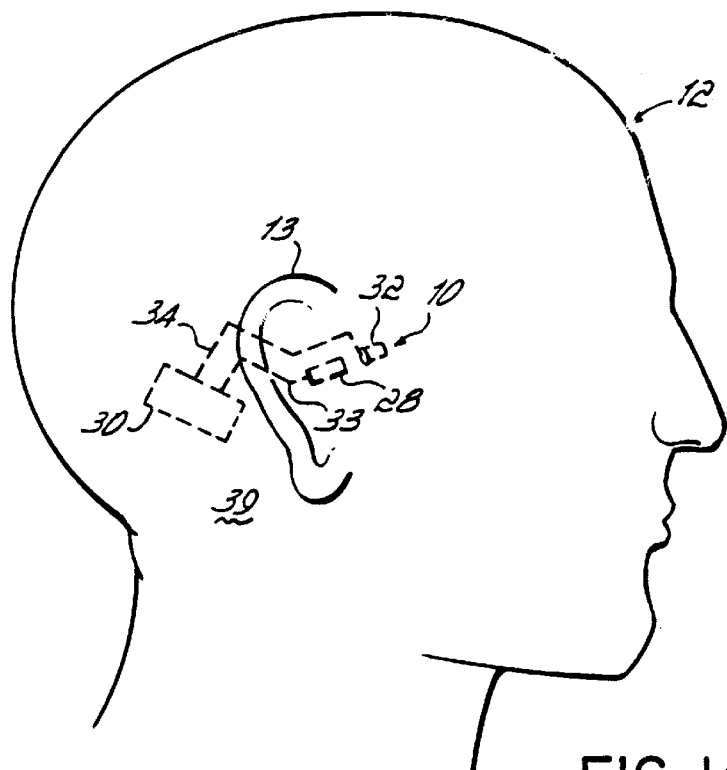
FIG. 1A is a schematic side view of the subject depicted in FIG. 1.

FIG. 1a is a side-view of the subject 12 which depicts the relative positions of the microsensor 28, the processor 30 and the microactuator 32 with respect to the external ear 13. The processor 30 is located subcutaneously so that instructions for operating the controls of this auditory system 10 may be signaled from outside of the subject 12. The microsensor 28 and the microactuator 32 are micromachined components and therefore are of such a small size as to require little or no destruction of human tissue of the subject 12 during surgical implantation. In fact, the micromachined microactuator 32 may be implanted via a presently used laser stapedotomy technique.

II. The Electrical System

Figure 2:
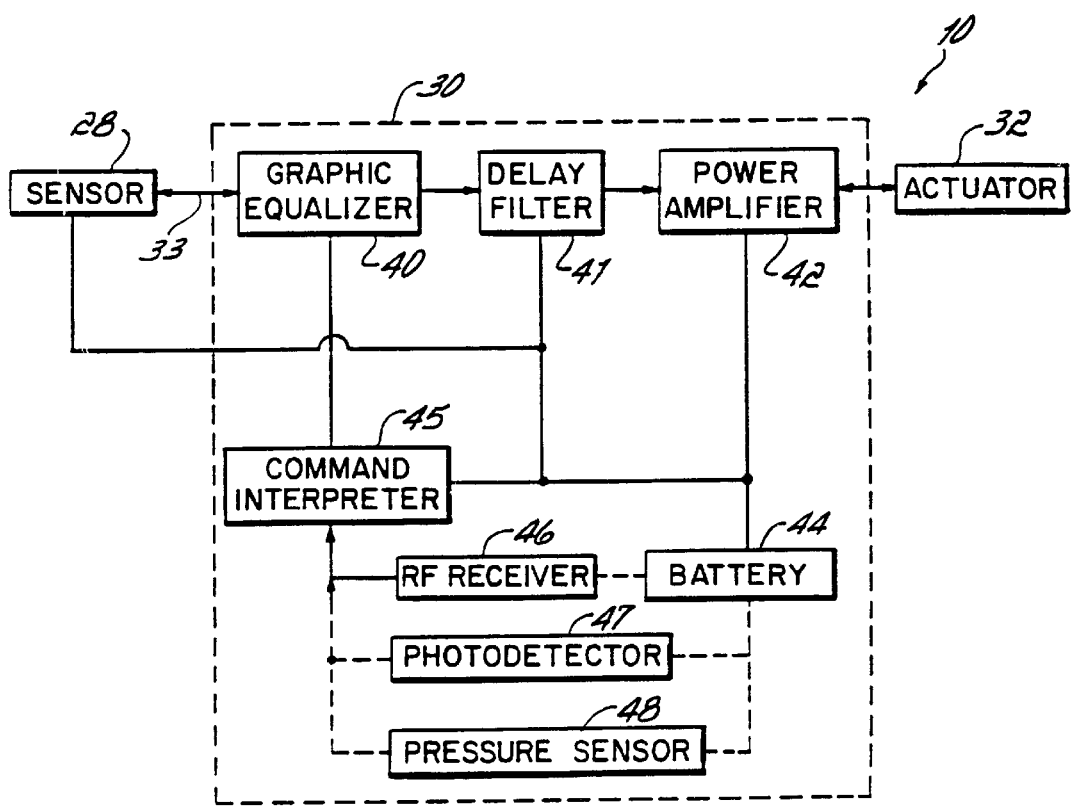
FIG. 2 is a block diagram which schematically depicts the electrical components of an auditory system constructed in accordance with the invention.

FIG. 2 schematically depicts the electrical interconnections among the components of this auditory system 10. More specifically, FIG. 2 shows that processor 30 includes a graphic equalizer 40, a delay filter 41 and a power amplifier 42. The graphic equalizer 40 preferably separates the electrical signals into three or more bandwidths of predetermined audio frequency ranges and also provides gain control of 0–32 dB for those bandwidths which include signals in the audio frequency range of 500–3500 Hz or more. The delay filter 41 performs phase shifting of the electrical signals, if necessary, by plus or minus 180 degrees to avoid constructive or destructive interference. The power amplifier 42 receives the phase shifted signals and amplifies these signals before they are transmitted via cable 34 to microactuator 32. The graphic equalizer 40, the delay filter 41 and a power amplifier 42 interconnect with the power source 44, which is preferably a five to six volt lithium battery, although simulated studies indicate that this voltage may eventually be reduced to three volts.

Each of these components also interconnects with a command interpreter 45 which is located close to the undersurface of the skin of the subject 12. The command interpreter 45 controls operations of the other components of the system 10. For instance, the command interpreter 45 controls the settings for the gain of the different bandwidths separated by the graphic equalizer 40. An initial setting may be made by "burning in" a ROM prior to surgical implantation, with the initial setting determined by the particular hearing characteristics and/or deficiencies of the subject 12. If desired, these settings may be made variable by a physician or an audiologist, preferably by using an EPROM to minimize surgical procedures. The command interpreter 45 also controls the power amplifier 42 and the power source 44 to increase or decrease the volume or to turn electrical power to the auditory system 10 off or on, respectively.

The command interpreter 45 controls the other components in response to instructions received from outside the subject 12. These instructions may be input via receipt of coded RF signals by a RF receiver 46, receipt of coded light signals by a photodetector 47 or receipt of a coded sequence of applied forces by a pressure sensor 48. If coded RF signals or coded light signals are used to instruct the command interpreter 45, a hand held RF transmitter (not shown) or an infrared transmitter (not shown) may be carried in the pocket of the subject 12, respectively. If the command interpreter 45 is instructed via pressure, the subject 12 instructs the command interpreter 45 by applying a coded sequence of forces, as with a finger, to the skin residing just outside of the pressure sensor 48.

Coding of the input signal reduces the possibility of inadvertent instructing of the command interpreter 45, as may occur, for example, via stray RF signals, stray light signals or forces applied to the head, such as the force of a tight fitting hat. Preferably, the command interpreter 45 and the other components of the processor 30 operate on lower power CMOS to eliminate the need for a standby current. Also, the processor 30 is preferably encapsulated in a biocompatible material such a silicone polymer.

III. The Microsensor

Figure 3:
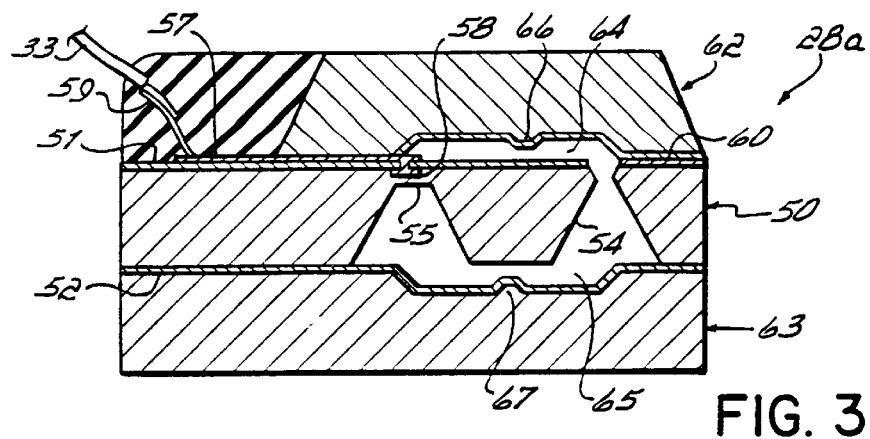
FIG. 3 is a cross-sectional schematic which depicts a first preferred embodiment of a microsensor used in an auditory system constructed in accordance with the invention.

FIGS. 3 and 3a depict a microsensor 28 constructed in accordance with a first preferred embodiment of the invention. More particularly, FIG. 3 depicts a microsensor 28a which comprises a piezoresistive vibration sensor micromachined out of a single semiconductor crystal or substrate 50 of n-type material. The crystal 50 is most likely silicon, though galium arsenide may also be suitable. The crystal 50 is etched from a top surface 51 and from a bottom surface 52 to provide an inertial or seismic mass 54 cantilevered by two parallel support arms 55, as shown in FIG. 3a. Five conductive metallic electrodes 57 are deposited on the top surface 51 of crystal 50 by electron beam evaporation or any other suitable deposition or metallization technique. Preferably, four p-doped piezoresistive regions 58 reside beneath the ends of the conductors 57, at the support arms 55, to form an integrated Wheatstone bridge for sensing vibration of the seismic mass 54. Electrical leads 59 connect to electrodes 57 to provide power and to convey a generated electrical signal to and along cable 33. Preferably, a passivation layer 60 resides adjacent the top surface 51 of the crystal 50.

If desired, additional trimming resistors 58a for temperature compensation may be deposited on crystal 50. Additional metallization, designated generally by reference numeral 57a, may be used to vary or control the steady state current through piezoresistors 58 via interconnection with resistors 58a. Contacts 57b enable the crystal 50 to be tested for diffusion, and electrical contact 57b connects directly with the crystal 50.

With this microsensor 28 mounted to one of the bones of the ossicular chain 21, mechanical vibrations of the ossicular chain 21 and/or the eardrum 15 also cause movement of the seismic or inertial mass 54. Forces applied to the support arms 55 by movement of the inertial mass 54 generate changes in the resistance of the piezoresistors 58, thereby resulting in change in current along the conductors 57.

Preferably, the microsensor 28a is hermetically sealed between upper and lower caps 62 and 63, respectively. Each of the caps 62 and 63 includes an etched depression, 64 and 65, respectively, which permits the inertial mass 54 some freedom of movement but also act as an air damper. The depressions 64 and 65 each include raised centers 66 and 67, respectively, which limit movement of the inertial mass 54 to prevent breakage. Because of the extremely small sizes which may be achieved through micromachining techniques of the type used to form this microsensor 28a, the mass of this microsensor 28a may be as low about 20 mg. This microsensor 28a is more completely described in a Doctoral Dissertation entitled "DEVELOPMENT OF A FULLY INTEGRATED MICROMACHINED PIEZORESISTIVE ACCELEROMETER/VIBRATION SENSOR WITH INTEGRAL AIR DAMPING FOR CONDITION MONITORING", and presented in 1992 by Kevin M. Walsh, which is expressly incorporated herein by reference, in its entirety.

Figure 4:
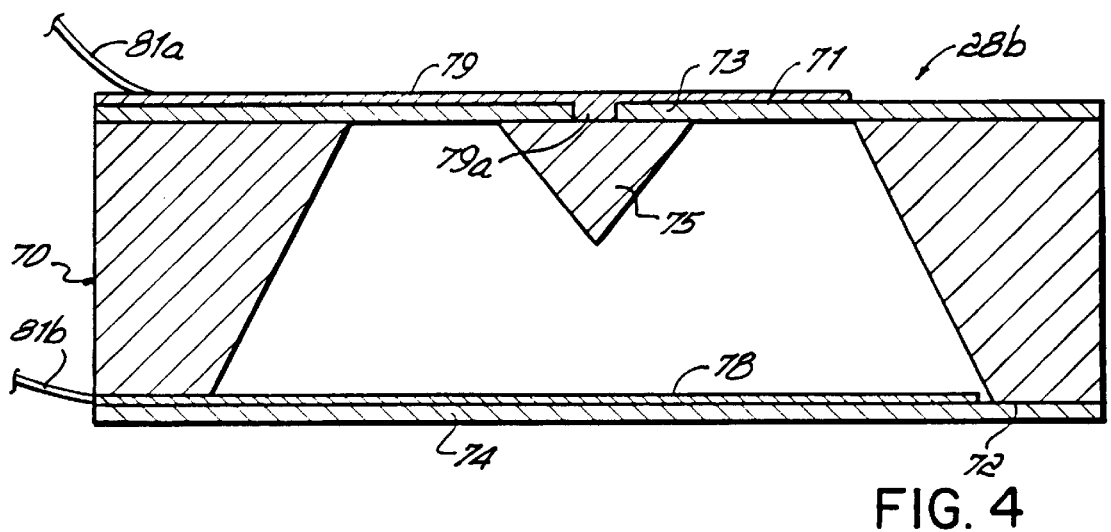
FIG. 4 is a cross-sectional schematic which depicts a second preferred embodiment of a microsensor used in an auditory system constructed in accordance with the invention.

FIGS. 4 and 4a depict a microsensor 28 constructed in accordance with a second preferred embodiment of the invention. More particularly, FIG. 4 depicts a micromachined capacitive microsensor 28b for sensing mechanical vibrations and converting the mechanical vibrations to electrical signals. The microsensor 28b is micromachined out of a single semiconductor crystal 70 such as silicon with a <100> orientation. A top surface 71 of the crystal 70 is passivated to form an electrically insulative layer 73 of either silicon dioxide, $SiO_2$, or silicon nitride, $Si_3N_4$, and a central portion of a bottom surface 72 is etched all the way through to remove all but the top layer 73 and a central inertial mass 75 or hillock.

A substrate 74 is bonded to the bottom surface 72 to enclose the etched space of the crystal 70. If made of glass, the substrate 74 is electrostatically bonded to surface 72. A conductive capacitor electrode layer 78 of aluminum or gold is deposited on the inside surface of the substrate 74. Alternatively, layer 78 may be polycrystalline silicon on glass or the substrate 74 may be single crystalline silicon electrostatically bonded across a glass or silicon dioxide $SiO_2$ surface to the base crystal 70. Preferably, the conductive layer 78 covers the area that was etched from bottom surface 72. The conductive layer 78 ultimately connects to a lead 81b electrically connected to the bottom surface 72 of the crystal 70, similar to the electrical connection shown for the sensor in FIG. 3.

A metallization film 79 covers top surface 71, and another electrical lead 81a is bonded to the metallization film 79, which serves as the upper capacitive electrode. The leads 81a and 81b are aluminum or preferably gold, which is biocompatible. The leads 81a and 81b connect to electrical wires carried within cable 33 (not shown). The hillock 75 may be electrically connected to the conductive layer 79, via region 79a, as shown in FIG. 4, or the hillock 75 may be isolated from layer 79 by extending layer 73 all the way across crystal 70.

With a voltage applied to leads 81a and 82b, this microsensor 28b acts as a parallel plate capacitor, with layer 78 acting as one plate and film 79 and hillock 75 acting as the other plate. When mounted to one of the bones of the ossicular chain 21, mechanical vibrations of the ossicular chain couple into the hillock 75 as an inertial or seismic mass which will cause relative movement between hillock 75/electrode 79 and substrate 74 to produce capacitance fluctuations. These capacitance fluctuations are detected by conductive leads 81a and 81b and may be converted to voltage signals to be conveyed to the processor 30 via cable 33.

Compared to a piezoresistive sensor, a micromachined capacitive microsensor 28b of this type requires less electrical current. This results in extended life for the battery 44 for this implanted auditory system 10.

The particular microsensor 28b shown in FIG. 4 works best when mounted to the ossicular chain 21 and used as a vibration sensor for detecting mechanical vibrations thereof. Alternatively, the microsensor 28b may be micromachined without a hillock 75 and mounted anywhere in the middle ear 16 to act as an acoustical microphone, rather than as a vibration sensor. When used as an acoustical microphone for sensing air pressure waves, performance is optimized if the plates are as thin and uniform as possible, thereby to maximize relative movement therebetween.

Figure 5:
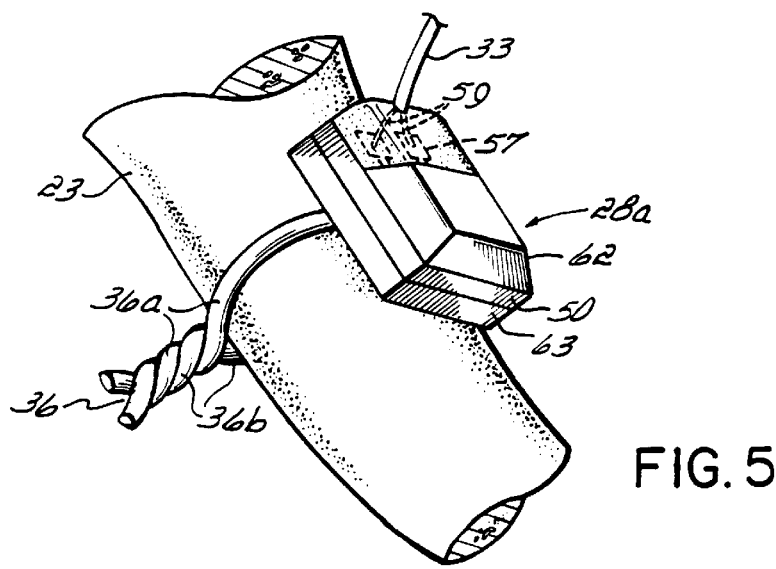
FIG. 5 is an enlarged schematic perspective view which depicts securement to the incus of a microsensor used in an auditory system constructed in accordance with the invention.

FIG. 5 shows microsensor 28a or 28b secured to the incus 23 via crimped wires 36a and 36b.

IV. The Microactuator

Figure 6:
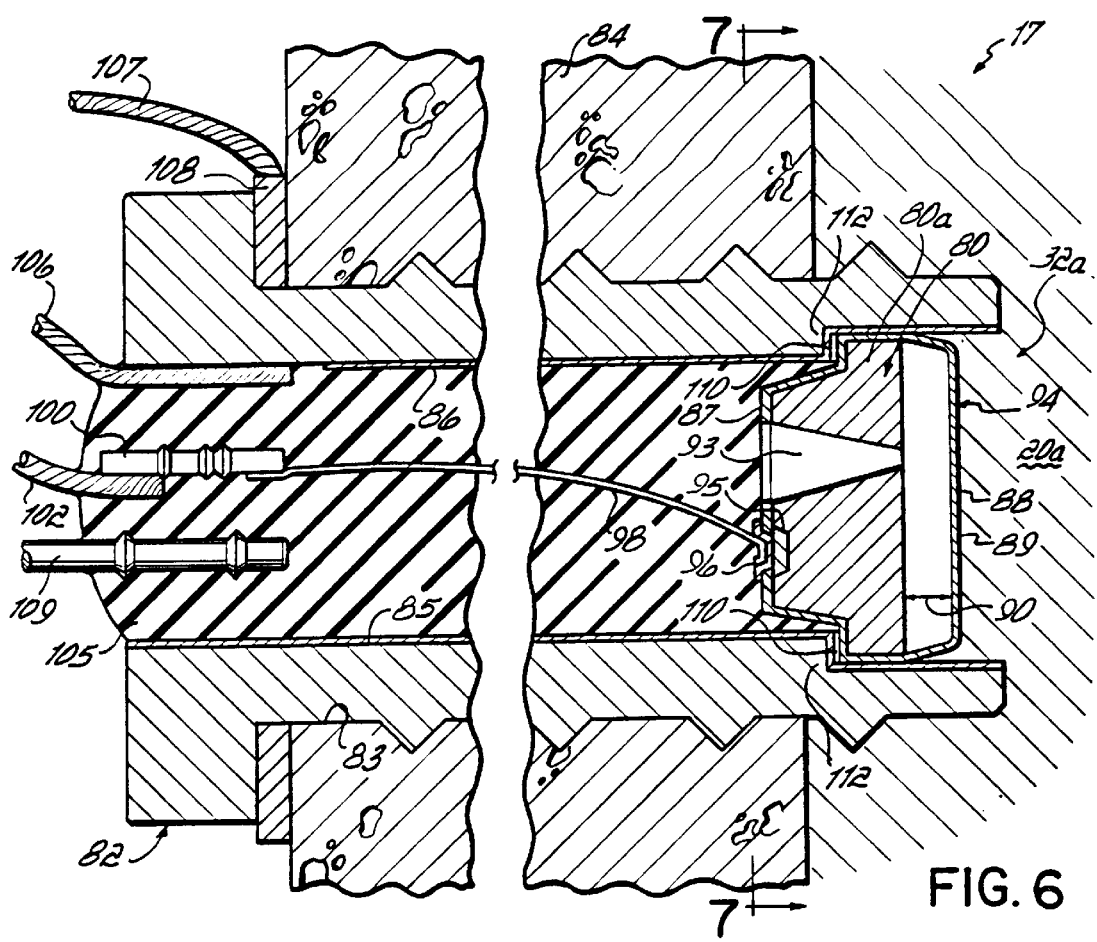
FIG. 6 is a cross-sectional schematic view which depicts a first preferred embodiment of a microactuator for vibrating fluid in the inner ear in accordance with the invention.

FIG. 6 is a cross-sectional schematic view which depicts a microactuator 32 implanted in the subject 12 in accordance with a first preferred embodiment of the invention. More particularly, FIG. 6 depicts a microactuator 32a located within an externally threaded screw 82 which is threaded into a surgically formed fenestration 83 in the promontory bone 84 of the subject 12. The screw 82 preferably has an outside diameter of about 2 mm. Alternatively, the fenestration 83 may be formed in the footplate 27 of the stapes 24. The fenestration 83 may be formed by present surgical laser techniques or by drilling, depending upon whether the fenestration is formed in the footplate 27 or the promontory 84, respectively. The threads are unnecessary if the fenestration is formed in the footplate 27.

Preferably, the screw 82 is made of gold alloy or of gold so as to be biocompatible, and the screw 82 has an insulative layer 86 coated along the inside surface of a bore 85 formed therethrough. The microactuator 32a is preferably formed from a single semiconductor crystal 80 of silicon with a crystalline orientation of <100> and doped to a resistivity of 10 ohm-cm or less and then mounted within a forward end of the bore 85.

The crystal 80 is micromachined through a top surface 87 thereof to form a flexible diaphragm 88 with an outer surface 89 which is in direct contact with the fluid 20a of the inner ear 17 after surgical implanting. The flexible diaphragm 88 is spaced from a remainder or major portion 80a of the crystal 80, with a space 90 located therebetween. The space 90 is actually an etched void having a thickness of about one to five microns, and this etched void 90 is etched via access holes 93 (FIG. 7) which extend from top surface 87 and through portion 80a.

The void 90 represents the volume previously occupied by a sacrificial layer formed on the bottom of crystal 80 prior to formation of a passivation layer. The sacrificial layer must be formed of a material which is susceptible to an etchant which does not etch the major portion 80a and the diaphragm 88. The actual material used to form the sacrificial layer or the etchant may vary, depending upon the characteristics of the starting material, i.e. the crystal 80.

The flexible diaphragm 88 is actually one section of a passivation layer 94 of silicon dioxide or silicon nitride which extends completely around the external surface of the crystal 80. This passivation layer is electrically nonconductive. Diaphragm 88 is preferably 0.10 to 1.0 microns in thickness and has length and width dimension of about 1.0–1.5 millimeters×1.0–1.5 millimeters.

In one approach for micromachining microactuator 32a, the spacing or void 90 between the electrodes may be formed by a sacrificial layer etch-away technique. First, silicon dioxide is thermally grown on. the surface of the silicon wafer 80 to a thickness on the order of one to several microns (micrometers). Then circular silicon dioxide islands are photolithograhically formed by ordinary semiconductor patterning techniques, and the complete surface is coated with a layer 94 of silicon nitride (typically by reactive ion sputtering or low-pressure chemical-vapor-deposition) to a thickness on the order of one half to two microns. Part of this layer 94 serves as the lower vibrating membrane 88 of the micromachined capacitive microactuator 32a. The surfaces of the <100> silicon crystal 80 are processed using an appropriate combination of anisotropic (KOH, EDP or hydrazine) or isotrophic etching (typically nitric, hydrofluoric, acetic acid combination) to provide the access holes 93 for subsequently etching away the sacrificial silicon dioxide layer near the bottom side. For selectively removing the silicon dioxide sacrificial layer, the etchant will typically be a hydrofluoric acid solution. The access holes 93 take advantage of the nonetching <111> crystallographic planes using silicon anisotropic micromachining technology (or a plasma RIE may be used).

Several other combinations may be used for the sacrificial layer, such as n or n+ doped silicon surface (ion-implanted, pre-deposition thermally diffused or epitaxially grown) on top of a p+ silicon substrate which serves as an etch stop as well as a highly conductive electrode. In the latter case, an etchant access hole must be provided to the n or n+ layer, such as by reactive ion etching (RIE) through the p+ region. The lab experiences of one of the inventor's has revealed that an aqueous solution of hydrazine will preferentially etch the n+ region away, leaving the narrow space or void 90 necessary for movement of the diaphragm 88, even if the remaining body of the crystal is n type rather than p+.

The outer area of the screw 82 may contain slots for an insertion tool, flats or similar means for tapping the screw 82 through the bony tissue of the promontory 84. The screw 82 electrode may be soldered, welded or may consist of a contacting metal washer. The bottom of the screw 82 will extend below the delicate actuator membrane 88 to protect it during installation.

The diaphragm 88 may also comprise an electrochemically etch-stopped epitaxial layer of silicon (n on p or p on n). However, because of the small area required in this case, it is difficult to achieve the thinness necessary, i.e., 0.5 to 2 microns, for low voltage actuation without using silicon nitride or silicon dioxide membranes.

Figure 7:
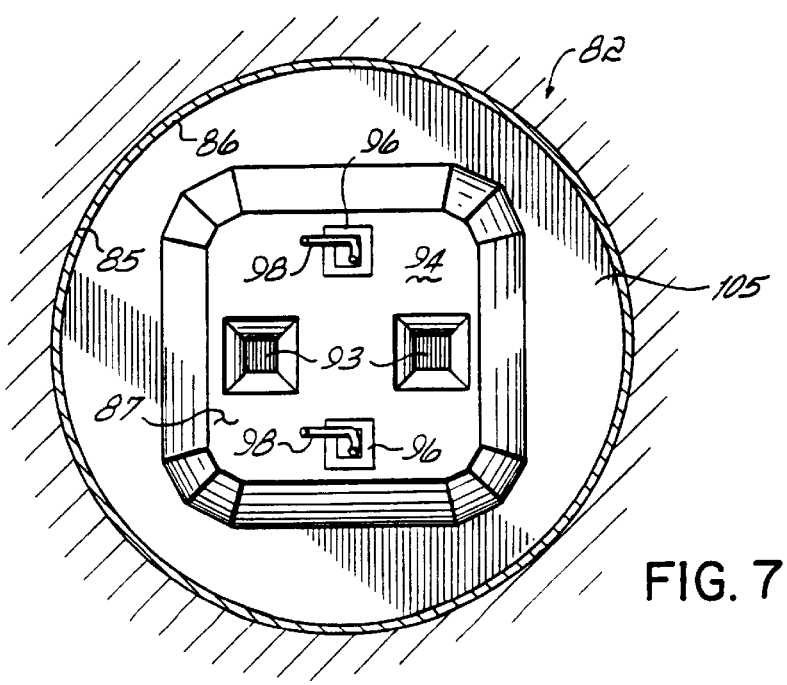
FIG. 7 is a cross-sectional schematic view of the actuator taken along lines 7—7 of FIG. 6.

FIG. 6 shows a degeneratively doped (n+ or p+) region 95 near top surface 87 to assure good ohmic contact between the silicon of portion 80a and an above metallized region 96 of aluminum, gold or copper, but this region 95 is not necessary if crystal 80 is highly doped. If the silicon crystal 80 is highly p+, it will also serve as an effective etch stop for ordinary anisotropic etchants (such as KOH or EDP). This region 96 is ultrasonically or thermocompression wire bonded to an aluminum or gold wire 98 which extends through the bore 85 and is interconnected to an electrical terminal 100, which is in turn connected to an electrode 102 which extends into cable 34. Preferably, the terminal 100 is made of copper or gold, and the electrode 102 is a gold wire or another electrically conductive material coated with teflon so as to be biocompatible. Preferably, as shown in FIG. 7, two electrical connection wires 98, are extended through screw 82 to assure electrical voltage transmission in the event that one of the wire 98 should fail. FIG. 7 also shows that two etched holes 93 are accessed to etch the void 90. The remainder of the inside of the screw 82 is encased within an encapsulant 105, such as silicone polymer.

This microactuator 32a acts as a very small parallel plate capacitor. The processor 30 conveys electrical voltage signals along electrode 102, via electrical terminal 100, wires 98 and connection regions 96 and 95 to the major portion 80a of crystal 80, which acts as one of the conductive plates of the parallel plate capacitor.

One important aspect of this microactuator 32 relates to the use of the ionic nature of the fluid 20a of the inner ear 17 as the other plate of the micromachined capacitor, with the spacing between "plate" 80a and the other "plate", i.e. the inner ear fluid 20a, defined by the combined thickness of the diaphragm 88 and the etched void 90 residing therebetween. The body of the screw 82 itself serves as an electrode for supplying electrical voltage signals to the fluid of the inner ear 17. A first electrode 106 extends into the bore 85 of the screw 82 and is soldered or welded thereto. If desired, an alternative electrode 107 may be soldered or welded to a washer 108 residing between the head of the screw 82 and the promontory 84. If no washer 108 is used, the alternative electrode 107 may be soldered directly to the head of the screw 82. If desired, a mount 109 may also extend from screw 82 for mounting the microsensor 28 thereon for acoustical pickup from the structure or the surrounding air of the middle ear.

Electrical voltage signals applied to portion 80a and the fluid 20a of the inner ear 17 generate electric fields across space 90 and diaphragm 88. Because of the very small dimensions of space 90 and diaphragm 88, i.e. six microns at most, relatively small applied voltages will generate large electric fields. The magnitude of the generated electric fields causes electrostatic forces to act on the diaphragm 88, resulting in mechanical vibrations. These diaphragm 88 vibrations directly stimulate or vibrate the fluid of the inner ear 17. The vibrations of the fluid 20a of the inner ear 17 actuate the receptor cells 20b to cause the nerve fibers 20c to signal the brain of the subject 12 to perceive the electrical voltage signals as sound.

For this approach, it is important to maintain good electrical isolation between portion 80a and screw 82, which acts as one of the electrodes and conveys electrical signals to the fluid of the inner ear 17. To accomplish a bond while maintaining this electrical isolation, an additional layer 110 of low melting point glass or another sealant material is preferably deposited between the passivation layer 94 and the screw 82 at a point 112 where the bore 85 has a slightly increased diameter for receiving the microactuator 32a. The glass film 110 may be deposited by chemical vapor deposition. The passivation layer 94 also provides electrical isolation. It is believed that the passivation layer 94 and the layer 112 will sufficiently isolate portion 80a from the fluid 20a of the inner ear 17. Other polymeric sealing methods can be used, if necessary. It is desirable for the silicon crystal 80 to be as highly conductive as possible (e.g. p+) because it serves as the inner or upper capacitive electrode.

If it is necessary to assure better electrical isolation, the screw 82 may be made of teflon, an electrically insulative material, with an external coating of electrically conductive material such as gold deposited thereon. According to this alternative approach, one or both of the electrodes 106 and 107 are then bonded to the external surface of the screw 82.

Although the diaphragm 88 could, in principle, be electrically insulated from the perilymph 20a by utilizing electrical contacts anisotropically etched through the crystal 80, this would be difficult because of the limited space. As stated previously, the outside diameter of the screw 82 is about 2 mm in diameter, and the actuator 32a must fit within the body of the screw 82.

Figure 8:
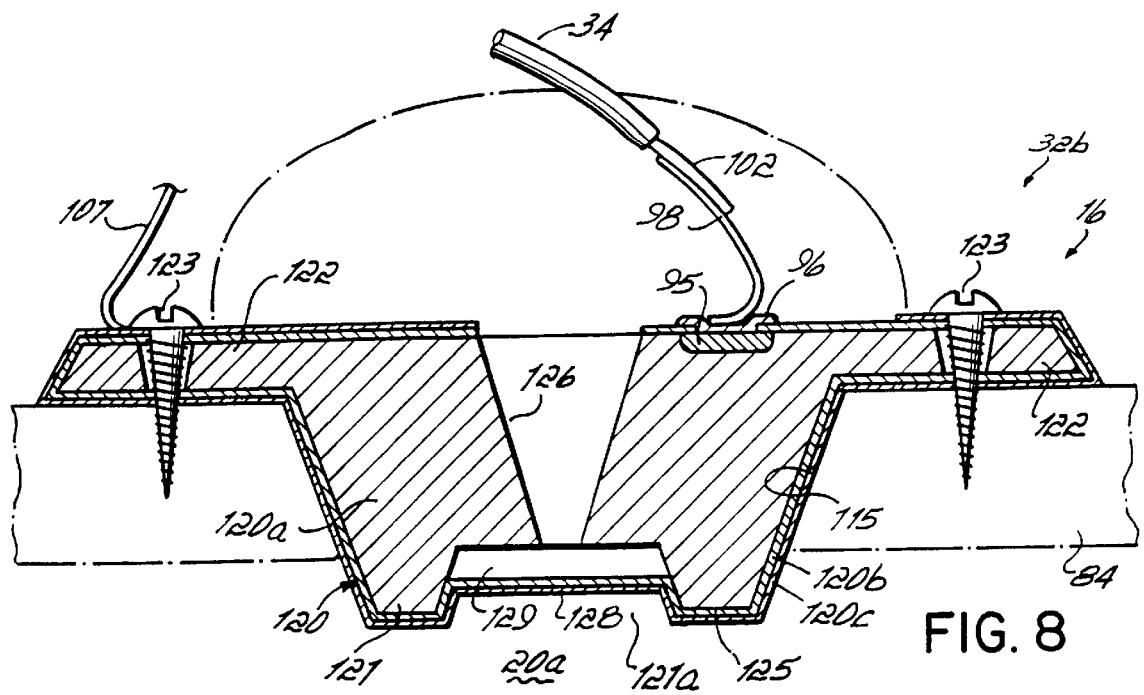
FIG. 8 is a cross-sectional schematic which depicts a second preferred embodiment of a microactuator for vibrating fluid in the inner ear in accordance with the invention.
Figure 8A:
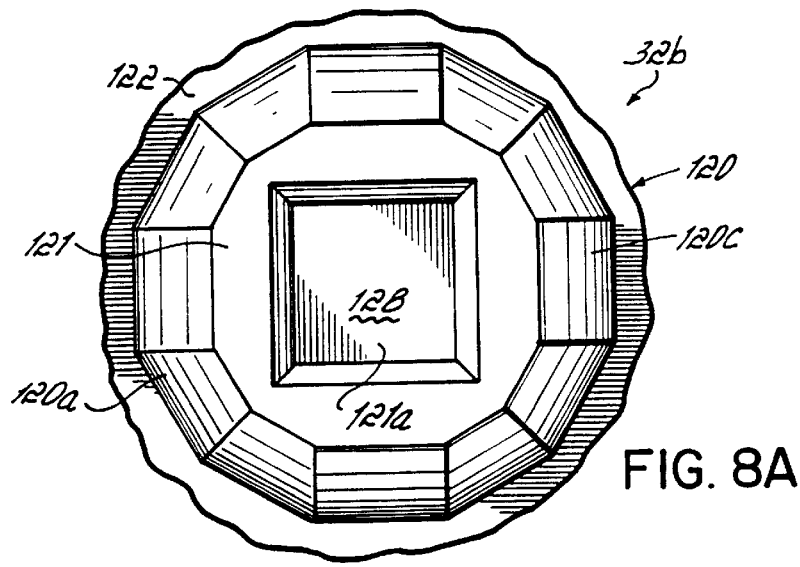
FIG. 8A is a bottom view of FIG. 8.

FIG. 8 is a cross-sectional schematic which depicts a microactuator 32 implanted in the subject 12 in accordance with a second preferred embodiment of the invention. More particularly, FIGS. 8 and 8a depict a microactuator 32b which is mounted within a tapered hole or fenestration 115 formed in the promontory 84, as by drilling.

The microactuator 32b includes a semiconductive crystal 120 of 10 ohm-cm resistivity or less which is <100> crystalline orientation and micromachined, i.e. etched, in this case, to form a tapered, twelve sided shape which may be further rounded by a final isotropic etch if necessary. This shape is dictated or defined by etching a crystal with a <100> orientation. Fenestration 115 is circular and tapered, and is formed by a circular tapered drill. Because the fenestration 115 is circular, it is desirable to shape the crystal 120 so that it closely approximates a circle. The microactuator 32b includes a flange portion 122 which is integral with crystal 120, and the flange shape 122 is formed by selectively etching from the top and the bottom. Miniaturized screws 123 secure the flange 122 to promontory 84 around the outside of the fenestration 115. The crystal 120 is selectively etched from a bottom surface 125 to leave an outer protective rim 121 which surrounds a recess 121a. A sacrificial later of selectively unformed thin dimension, i.e., one to five microns, is then formed within the bottom of the recess 121a (or the top, as viewed in FIG. 8), and the crystal 120 is then passivated around its entire external surface.

At least one access hole 126 is then etched from the top surface 124 to the bottom surface 125 of the crystal 120, and then the access hole 126 is used to etch away the sacrificial layer, in much the same manner that void 90 was formed in microactuator 32a, thereby leaving a flexible diaphragm 128 and a major portion 120a of crystal 120 separated by a space or void 129 which is one to five microns thick. The diaphragm 128 preferably has the same thickness as diaphragm 88 and the diameter of the diaphragm 88 is about the same dimension as the diagional span of rectangular diaphragm 128. Void 129 occupies the volume formerly occupied by the sacrificial layer. Electrical interconnection can then be made between internal major portion 120a and cable 34, so that portion 120a acts as one "plate" of a micromachined parallel plate capacitor.

The bottom surface 125 of the diaphragm 128 resides in direct contact with the perilymph fluid 20a of the inner ear 17. An outer passivation layer 120b or surface of crystal 120 may be coated with a metallization layer 120c in selected regions. Thus, the fluid 20a of the inner ear 17 may serve as the other "plate" of the micromachined parallel plate capacitor, if layer 120c does not cover layer 120b at diaphragm 128. Alternatively, if the layer 120c does cover the diaphragm 128, this portion of layer 120c acts as the other "plate". For either approach, the electrical interconnection of the fluid 20a to cable 34 may be via an electrical lead 107 attached beneath screw 123 or bonded to a washer (not shown) located beneath screw 123.

Alternatively, a throughhole may be etched through crystal 120 from top surface 124 to bottom surface 125 and then a microactuator of the type depicted in FIG. 6 may be physically located inside the throughhole. In this manner, the crystal 120 would simply serve as a housing for the microactuator, similar to the function formed by the screw 82 depicted in FIG. 6.

FIGS. 9 and 9A are schematic cross-sections which depict two variations of a third embodiment of a microactuator 32 in accordance with the invention. More particularly, FIG. 9 depicts a microactuator 32c which utilizes electrostatic actuation for directly vibrating the fluid in the inner ear 17, and microactuator 32c is a micromachined parallel plate capacitor similar to microactuators 32a and 32b, but microactuator 32c does not utilize the perilymph fluid 20a as one of the "plates".

A semiconductor crystal 130 of <100> crystalline orientation and 10 ohm-cm or less resistivity is selectively micromachined to form a parallel plate capacitor with a conductive diaphragm 132 which is preferably made of polysilicon film. The flexible diaphragm 132 is located in the middle ear 16, outside of a fenestration 131 formed in the promontory 84. A piston 134 connects to the diaphragm 132, as by a screw 135. The head of the screw 135 is eutectically bonded to diaphragm 132, or by a direct gold silicon bond 136 formed therebetween. Piston 134 is preferably gold plated metal, silicon dioxide fiber or teflon. The diameter of the fenestration 131 and the piston 134 must be close enough to prevent leakage of fluid 20a. The conductive diaphragm 132 is supported by a flange-shaped portion of crystal 130 which includes an electrically insulating region or interior shell 138 which is selectively coated, i.e., metallized, on its outside surface by a conductive region 140 which conveys electrical signals to the conductive diaphragm 132. Vibration of the flexible diaphragm 132 causes piston 134 to vibrate, thereby directly stimulating the fluid 20a of the inner ear 17.

In this approach, compared to microactuators 32a and 32b, the diameter of fenestration 131 may be, reduced, which may be advantageous medically. Moreover, the cross-sectional area of the two plates is also increased, which promotes stronger electrostatic actuation forces. This embodiment of the invention is advantageous in instances where access to promontory 84 is limited, or for one reason or another it is desirable to surgically form a fenestration 130 with a reduced diameter and/or to enlarge diaphragm area. The piston 134 will be sealed from leakage of perilymph fluid by employing standard techniques presently used for mechanical prostheses.

FIG. 9a shows another variation of this approach. In FIG. 9a, a diaphragm comprises an electrically conductive outer layer 142, which is preferably polysilicon but may be gold, and on interior electrically insulating layer 138, as in FIG. 9.

Figure 10:
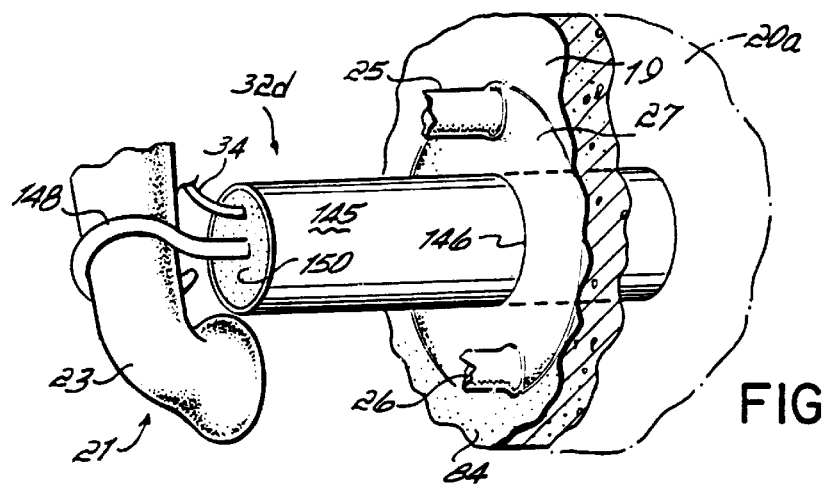
FIG. 10 is schematic perspective which depicts a fourth preferred embodiment of the microactuator for directly vibrating the fluid of the inner ear, wherein the microactuator connects to the incus and the stapes bones of the subject.

FIG. 10 depicts a microactuator 32 constructed in accordance with the fourth embodiment of the invention. More particularly, FIG. 10 depicts a microactuator structure 32d housed within a piston 145 which extends through a fenestration 146 surgically formed in the stapes footplate 27.

Present stapedotomy techniques, including laser surgery stapedotomy, include passive stimulation of the fluid 20a of the inner ear 17 via movement of a piston extended through fenestration in the stapes footplate and anchored to one of the bones of the ossicular chain. In this presently used technique, as described previously, vibrations of the ossicular chain 21 passively vibrate the fluid 20a of the inner ear 17. FIG. 10 shows a wire crimp attachment 148 formed in the shape of a hook connected to the incus 23, and with upper portions of legs 25 and 26 removed from the stapes 25 to make room for the piston 145.

This aspect of the invention utilizes present stapedotomy techniques by incorporating a microactuator of the type depicted in FIG. 6 or FIG. 8 into the piston 145, which is shown in FIG. 10, so that in addition to passive transmission of mechanical vibrations to the fluid 20a of the ear 17, this microactuator structure 32d also amplifies these mechanical vibrations. The components of microactuator structure 32d which are housed inside of piston 145 are encapsulated therein with a coating of biocompatible material such as silicone polymer 150. As with microactuators 32a and 32b, for microactuator structure 32d the housing, i.e., the surfaces of the piston 145, may be used as an electrode to convey electrical signals to the ionic fluid 20a of the inner ear 17.

The primary advantage of this approach relates to the fact that it utilizes a surgical technique which has been approved by the FDA of the United States Government and is currently used by a number of audiologists presently practicing in the United States.

Figure 11:
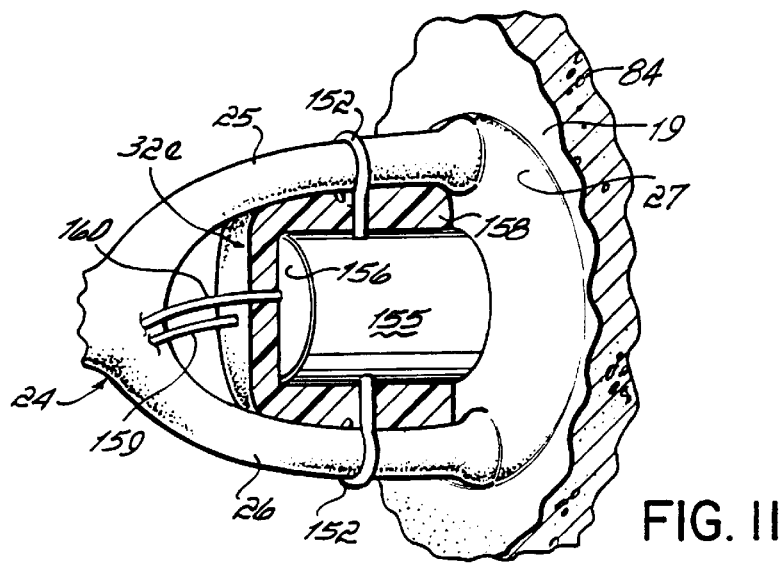
FIG. 11 depicts a fifth preferred embodiment of the invention wherein a microactuator indirectly vibrates the fluid of the inner ear through the stapes footplate but is not inertially grounded to the promontory of the subject.
Figure 12:
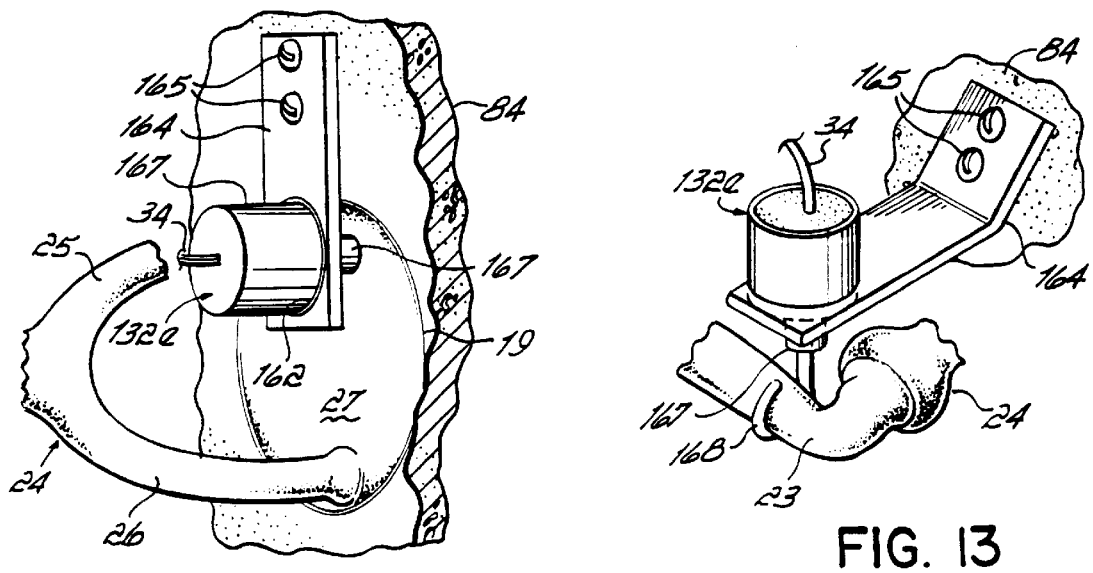
FIG. 12 depicts a variation of the fifth embodiment of the invention shown in FIG. 11, wherein a microactuator for indirectly vibrating the fluid of the inner ear is inertially grounded to the promontory of the subject so as to contact the stapes footplate.
Figure 13:
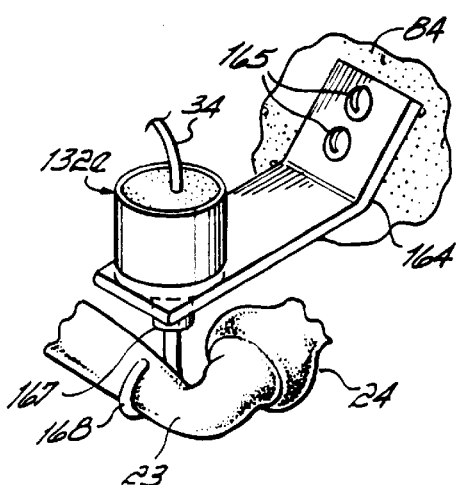
FIG. 13 depicts still another variation of the embodiment shown in FIGS. 11 and 12, wherein the microactuator which indirectly vibrates the fluid of the inner ear is mounted to the incus, and the microactuator is also inertially grounded to the promontory of the subject.

The previous four embodiments of the microactuator 32 rely upon direct vibration of the fluid 20a of the inner ear 17 via direct contact between the fluid 20a and a diaphragm or a piston secured to a diaphragm. FIGS. 11, 12 and 13 depict another approach of this invention which relies upon indirect stimulation or vibration of the fluid 20a of the inner ear 17. With indirect stimulation, the microactuator 32 includes a flexible diaphragm which vibrates in contact with one of the bones of the ossicular chain 21, thereby amplifying the normal mechanical vibrations of the ossicular chain 21. This approach is less surgically invasive then the other approaches which require the surgical forming of a fenestration.

FIG. 11 shows a microactuator 32e secured in contact with the stapes footplate 27 via wire retainers formed in the shape of hooks 152 connected to legs 25 and 26. Microactuator 32e is almost identical to microactuator 32d, but of a smaller length. Microactuator 32e includes a cylindrical housing 155 which houses the actuation components of the type depicted in FIG. 6. These components are located so that the diaphragm or a piston connected thereto is in contact with the footplate 27, and preferably spring-loaded into contact therewith. Vibration of the diaphragm will vibrate the footplate 27, thereby indirectly vibrating the fluid 20a. Encapsulative material 156 fills the remaining portion of the cylinder 155, and an outer coating 158 is sealed thereabout and may by itself be used as an alternate mounting technique. Electrical leads 159 and 160 supply electrical signals from cable 34 to microactuator 32e.

FIG. 11 depicts microactuator 32e in a non-inertially grounded condition because the microactuator 32 is simply connected to one of the bones of the ossicular chain 21. FIGS. 12 and 13 show variations of the fifth embodiment of this invention wherein microactuator 32e is inertially grounded to the promontory 84. More specifically, FIG. 12 shows microactuator 32e attached or bonded via a hole 162 to one end of a plate 164. Screws 165 anchor the other end of the plate 164 to the promontory 84. In this variation of the fifth embodiment, vibrations of the diaphragm of the microactuator 32e vibrate a piston 167 which is secured thereto, thereby vibrating the footplate 37 and stimulating the fluid 20a of the inner ear 17.

FIG. 13 shows microactuator 32e inertially grounded to the promontory via plate 164, using screws 165. A wire 168 formed in the shape of a hook encircles a portion of the incus 23 and connects the diaphragm to the incus 23 via piston 167. Again, vibrations of the diaphragm of the microactuator 132e vibrate the piston 167. Vibrations of the piston 167 are translated to the incus 23 via the wire 168, thereby to amplify the natural vibrations of the incus 23, which vibrations are then transmitted via the stapes 24 to the fluid 20a of the inner ear 17.

With the variation of the invention depicted in FIG. 13, the incus 23 and the stapes 24 must be interconnected in normal fashion. For the variation of the invention depicted in FIG. 11, while it is desirable that the other bones of the ossicular chain 21 remain intact, it is not absolutely necessary because the microactuator 32e is mounted directly to the stapes 24. For the variation of the invention depicted in FIG. 12, one of the legs 26 of the stapes 24 must be surgically removed.

Figure 14:
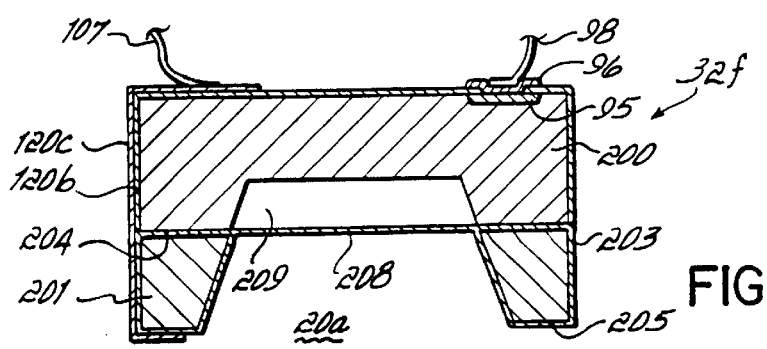
FIG. 14 is a cross sectional view of a microactuator in accordance with another embodiment of the invention.

FIG. 14 shows a microactuator 32f formed from two crystals 200 and 201. Crystal 201 is passivated with silicon mitride on its bottom surface 203. Both crystals 200 and 201 are etched on respective top surfaces, 204 and 205, to leave a diaphragm 208 of crystal 201 located above a void 209 in crystal 200. The crystals 200 and 201 are then bonded together. Electrical connection is made to crystal 200, which acts as one of the plates, and the crystal 201 is mounted so that diaphragm 208 is in contact with the perilymph 20a.

These various approaches of this invention provide a wide range of versatility for the surgeon in implanting the microactuator 32 in a subject 12 to overcome a hearing deficiency, for almost any type of ear anatomy, whether normal or abnormal.

While several preferred embodiments have been described, it is to be understood that applicant does not wish to be limited thereby. Numerous variations of the components of the invention may be possible, depending upon the type of hearing deficiency and the anatomy of the ear of a particular subject. The invention in its broader aspects is therefore not limited to the specific details of the representative apparatus, methods and examples shown and described. Accordingly, departures may be made from such details without departing from the spirit or scope of applicants' general inventive concept.

What is claimed is:

1. A method for reducing conductive and/or sensorineural hearing deficiency in a human subject comprising the steps of:

implanting a microactuator into a fenestration that pierces a promontory or a stapes footplate which respectively separate a middle ear from an inner ear of the human subject, the microactuator including a flexible diaphragm that contacts fluid present within the inner ear of the human subject, and that vibrates responsive to application of an electrical signal to the microactuator; and conveying an electrical signal to the microactuator which excites vibrations in the flexible diaphragm thereof, said flexible diaphragm vibrations stimulating the fluid of the inner ear of the human subject whereby the human subject perceives said flexible diaphragm vibrations as sound.

2. The method of claim 1 wherein the microactuator is formed with a threaded, right circular cylindrically-shaped outer surface about the flexible diaphragm, and wherein the microactuator is implanted into the fenestration that pierces the promontory by screwing the microactuator about the flexible diaphragm into the fenestration.

3. The method of claim 1 further comprising the step of implanting a processor for transmitting an electrical signal to the microactuator into a cavity surgically sculpted into a mastoid cortical bone of the human subject.

4. The method of claim 3 further comprising the step of implanting a microsensor, which responsive to impingement of acoustical pressure waves on the microsensor generates an electrical signal for transmission to the processor, into a cavity surgically sculpted into a mastoid cortical bone behind an ear of the human subject.

5. The method of claim 1 further comprising the step of implanting a microsensor, which responsive to impingement of acoustical pressure waves on the microsensor generates an electrical signal, into a cavity surgically sculpted into a mastoid cortical bone behind an ear of the human subject.

* * * * *